(12) United States Patent
Klein et al.

(10) Patent No.: US 6,565,550 B1
(45) Date of Patent: May 20, 2003

(54) LUER FITTING INJECTOR

(75) Inventors: Dean A. Klein, North Oaks, MN (US); James D. Brazil, Braham, MN (US); Daniel A. White, Minnetonka, MN (US)

(73) Assignee: Carbon Medical Technologies, Inc., St. Paul, MN (US)

( * ) Notice: Subject to any disclaimer, the term of this patent is extended or adjusted under 35 U.S.C. 154(b) by 0 days.

(21) Appl. No.: 09/309,652

(22) Filed: May 10, 1999

(51) Int. Cl.[7] .............................................. A61M 31/00
(52) U.S. Cl. ...................................................... 604/506
(58) Field of Search ..................... 604/57–62, 239–243, 604/232, 500, 506, 272, 513; 128/898

(56) References Cited

U.S. PATENT DOCUMENTS

| | | | |
|---|---|---|---|
| 4,490,142 A | * 12/1984 | Silvern | ........................ 604/241 |
| 5,242,419 A | * 9/1993 | Kiner et al. | ................. 604/195 |
| 5,441,487 A | 8/1995 | Vedder | |
| 5,743,883 A | 4/1998 | Visconti | |
| 5,785,693 A | 7/1998 | Haining | |
| 5,792,478 A | 8/1998 | Lawin et al. | |
| 6,063,062 A | 5/2000 | Paradis | |

* cited by examiner

Primary Examiner—Anhtuan T. Nguyen
(74) Attorney, Agent, or Firm—Nawrocki, Rooney & Sivertson, P.A.

(57) ABSTRACT

An improved Luer-lock fitting for hypodermic needles and methods for using the fitting to inject suspended solids into a body. The improved fitting includes a lumen having a curvedly tapered, distally decreasing throat region, which is believed to provide improved flow of suspended solids into the hypodermic needles. One fitting includes at least two threads to provide a more secure fitting able to withstand higher injection pressures. Another fitting includes rounded wings better able to withstand jarring by endoscope eyepieces and resisting being dislodged from position. One method includes injecting suspended solids into soft tissue such as sphincter mechanisms. One method includes injecting suspended solids into tissue surrounding a mechanism to correct defects.

4 Claims, 1 Drawing Sheet

LUER FITTING INJECTOR

FIELD OF THE INVENTION

The present application is related to devices and methods for injecting suspended solids into a body. Specifically, the present invention is related to a hypodermic needle assembly and hub having a curvedly tapered lumen and higher pressure Luer-lock fittings for joining syringes to hypodermic needles, and methods for using same.

BACKGROUND OF THE INVENTION

Hypodermic needles are commonly used to inject fluids into a body. It will be understood that injection of fluids occurs both with respect to human bodies and animal bodies. While the present invention, in its preferred embodiment, is intended for use in injecting fluids into a human body, veterinary applications are specifically contemplated. The needles have a sharpened distal end and often have a hub fitting on the proximal end for mating to a syringe. The fitting is often a Luer fitting, which describes generally the male-female shapes of the syringe and needle hub, respectively. When the Luer fitting includes means such as threads for locking the male and female parts together, the fitting is known as a Luer-lock tip. The Luer-lock fitting is a standard fitting in the medical field, often having a single thread having nominally three turns about the longitudinal axis of the syringe. The Luer-lock fitting is well suited for administering agents such as drugs through common hypodermic needle lengths.

A composition and method for treating urinary incontinence is described in related U.S. patent application Ser. No. 08/676,592, filed Jul. 8, 1996, entitled IMPROVED TISSUE INJECTABLE COMPOSITION AND METHOD OF USE, herein incorporated by reference. The composition includes solid particles having an average size of between about 100 and 1,000 microns, preferably between 200 and 500 microns. The particles can be carried in a suspension such as a fluid or gel.

Standard Luer-lock fittings have been used to inject the particles into a body through the employment of endoscopes, but with less than optimal results due in part to problems related to the particular application. One problem is the long needle lengths required for the application. Needle lengths are dictated both by anatomy and by the length of endoscopes used in the procedures. Needles used in injecting solids into the urinary sphincter muscles are nominally 16 inches long. Needles used in injecting solids into esophageal sphincter can be about 60 inches long. The longer internal paths have a higher resistance to flow than the shorter paths typically found in hypodermic needles.

Another problem is related to the nature of the injected composition. The injectable material includes solid particles suspended in a carrier, such as a gel. A typical Luer-lock fitting includes a lumen having a large inside diameter proximal end and a smaller inside diameter distal end. The transition from large inside diameter to small inside diameter can be a step change or a straight taper, as the shapes are easy to mold and manufacture. These transition taper shapes work well with typical liquids, but work less than optimally with large particles suspended in a liquid carrier. In particular, the particles can be swept along a straight taper region to a location immediately proximal of the small inside diameter portion, and become bunched up at this point. The particles massed at one point can prevent the further passage of any particles. What would be desirable is a Luer-lock fitting better able to lessen the blockage by the large particles.

Still another problem with conventional Luer-lock fittings is the use of a single thread. Attempting to force large, possibly bunched, suspended particles suspended in a viscous carrier through long hypodermic needles can require high pressure. In practice, this can require a great deal of hand pressure on the plunger of a syringe. In practice, this high pressure can result in fluid leakage at the Luer-lock fitting. The loss of the fluid can be a significant problem, as it serves as the carrier for the particles. With loss of the carrier in the Luer-lock fitting, the particles become more concentrated, and less likely for flow through the fitting and into the hypodermic needle lumen. What would be desirable is a fitting better able to withstand the high pressures required to inject suspended solids through hypodermic needles.

SUMMARY OF THE INVENTION

The present invention includes a hypodermic needle having an improved Luer-lock fitting for injection of suspended solids through the needle. The present invention includes methods for using the improved fitting to inject solid particles suspended in a viscous carrier through long hypotube sections and into soft tissue to treat deficiencies. Applicants believe the present invention reduces the blockage of Luer fittings by large, suspended solid particles. Applicants also believe the present invention provides a fitting better able to withstand the higher pressures applied when injecting viscous suspensions through long hypotube sections.

One improved fitting according to the present invention includes a substantially cylindrical or tubular hub body affixed to the proximal end of a hypodermic needle. The hub body has a proximal end for receiving fluid, a distal end for ejecting fluid, a lumen therethrough, and a hub body wall having a threaded region. The body includes a region having a curvedly tapered inside diameter, decreasing the inside diameter with increasing distal position. The curved taper region is preferably disposed distally of a standard, straight, Luer tapered region. The curved taper is believed to reduce the likelihood of blockage from particles bunching up near the taper distal end. Blockages have been observed in Luer fittings having straight tapers. Such blockages can preclude further particle flow and can cause large back pressures. Applicants believe even small blockages can preferentially allow flow of a suspension fluid over flow of suspended particles, concentrating the particles in less fluid until the blockage becomes more pronounced.

A preferred embodiment has more than a single thread, providing a tighter, pressure resistant seal between syringe and Luer-lock fitting. One fitting has two start threads 180 degrees opposed, each wrapping around the fitting for about 1 and ½ turns. One fitting hub has two opposed wings extending outward from the longitudinal axis of the hub. The wings provide a structure for tightly grasping and turning the hub relative to the syringe. Preferred wings have a rounded periphery. The rounded wings can deflect objects striking the wings, lessening the force which can act to dislodge a positioned hypodermic needle. In particular, the rounded wings can deflect an endoscope eyepiece knocking against the hub.

In use, a long hypodermic needle having a Luer-lock hub according to the present invention is provided. A suspension of solids in a liquid carrier is provided in a syringe adapted to mate to the Luer-lock fitting. The syringe is secured to the Luer-lock fitting at a point in time as dictated by the user. In one method, the syringe is secured before advancing the needle into the patient. In another method, the syringe is secured only after the needle tip has been advanced close to the target site. The needle is preferably advanced through an endoscope such that the sharp needle tip is visualized as the tip is advanced.

The sharp needle tip can be advanced until the target site is penetrated, and the syringe plunger depressed until a sufficient amount of solid suspension has been injected into the target. The needle can be retracted and advanced to different target sites until the area has been treated. A preferred use of the present invention is the augmentation of urinary, anal and gastric sphincter mechanisms with injected solid particles.

DETAILED DESCRIPTION OF THE PREFERRED EMBODIMENTS

Figure 1:
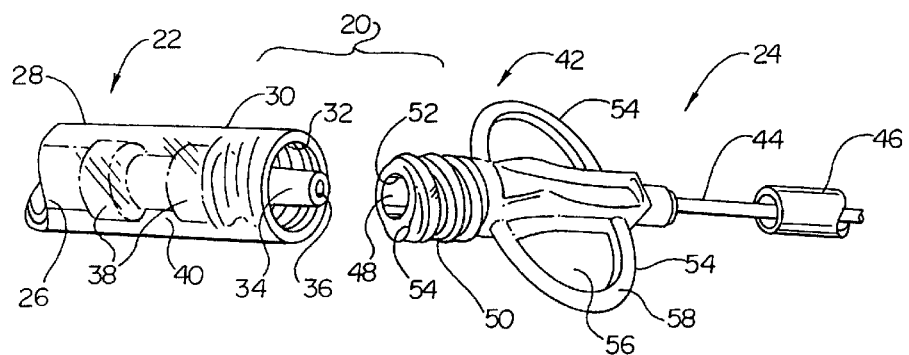
FIG. 1 is a perspective view of a system for injecting suspended solids, including a syringe and hypodermic needle with hub having a Luer-lock fitting and rounded wings.

FIG. 1 illustrates a system 20 for injecting suspended solids including a syringe 22 and a hypodermic needle assembly 24. Syringe 20 includes a generally cylindrical body 28 having a distal portion 30 and a threaded region 32. Disposed within syringe body 28 is a plunger 26 having a distal portion 40 and rubber seals 38. Syringe 22 has a tapered, protruding male member 34 having a lumen 36 therethrough. Member 34, in a preferred embodiment, has a standard Luer taper.

Hypodermic assembly 24 includes a proximal hub 42 and a needle 44. Needle 44 is commonly formed of hypotube and is illustrated having a protective sheath 46 disposed over needle 44. Hub 42 includes a threaded cylindrical region 50 having a lumen 48 therethrough. Lumen 48 substantially defines the longitudinal axis of hypodermic needle assembly 24. Threaded cylindrical region 50 includes an inner wall surface 52, preferably having a standard Luer taper adapted to mate with syringe member 34. In hub threaded region 50, a preferred embodiment has more than one start thread, to provide additional sealing force over the length of threaded regions 50 and 32 when tightened. In the embodiment of FIG. 1, hub threaded region 50 has two start threads, with one start indicated at 54 and the other disposed 180 degrees opposite. In this embodiment, each of the two threads wraps 1 and ½ turns about the hub. Some previous devices have utilized only a single thread which has sometimes proven less than optimal in retaining the suspension carrier fluid within the Luer-lock fitting under pressure. Other previous hub devices have utilized only protruding, stub-like ears in place of threads. These devices have sometimes proven unable to provide sufficient strength when a user attempted to provide a tight seal between syringe and hub. Hub 42 includes two wings 54, each having a thinner, internal portion 56, and a thicker, rounded, peripheral rib portion 58.

Figure 2:
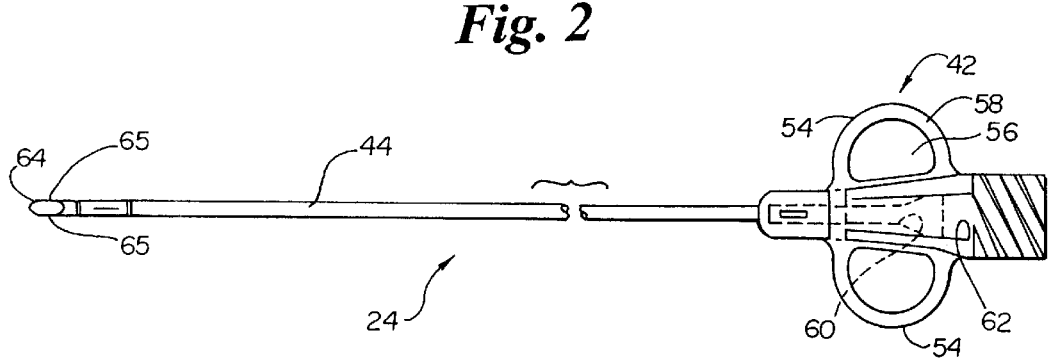
FIG. 2 is a top view of a the hypodermic needle and hub of FIG. 1.

Referring now to FIG. 2, hypodermic needle assembly 24 is further illustrated in greater detail. In a preferred embodiment, hub lumen 48 includes a Luer taper region 62 and a curvedly tapered region 60. Curvedly tapered region 60 is indicated by phantom lines in FIG. 2, illustrating the lumen through hub 42, which continues through needle 44. Needle 44 terminates in a distal skived portion 64. In a preferred embodiment, wings 54 are consistently oriented relative to skived portion 64. In one embodiment, wings 54 are oriented such that the widest portions of skived portion 64, as indicated at 65, are oriented outward in the same direction as wings 54. This orientation of skived portion 64 provides a predictable configuration that is consistent with the insertion of the needle tip through an endoscope while lessening the chance of wings 54 being dislodged by the endoscope eyepiece.

A preferred embodiment hub has wings to aid in securing a tight, pressure resistant fitting for the Luer-lock fitting. At least some prior art devices for injecting suspended solids have lacked wings. These device hubs have proven difficult to grasp tightly and held with latex gloved hands. The prior device drawbacks have sometimes lead users to affix clamps to the hypodermic hub in order to rotate the hub and syringe sufficiently tightly so as to form a tight seal. Wings 54 have a rounded periphery in a preferred embodiment, as illustrated in FIG. 2. The rounded periphery provides a rounded surface such that if another device, such as an endoscope eye-piece, collides with the wings, the other device can glance off the wings rather than connect squarely and risk dislodging a previously positioned needle tip.

Figure 3:
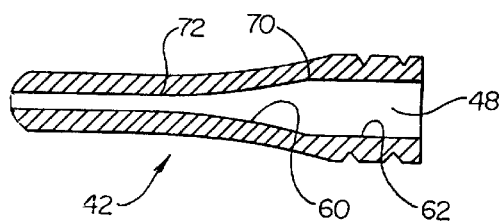
FIG. 3 is a longitudinal cross-sectional view of the Luer-lock hub fitting of FIG. 1 (with wings not shown), illustrating the curvedly tapered lumen region.

Referring now to FIG. 3, Luer taper 62 and curved taper 60 are illustrated in detail. In one embodiment, Luer taper 62 is a straight, ANSI taper, tapering from 0.170 inch inside diameter to 0.155 inch inside diameter over a length of 0.250 inch. In one embodiment, curved taper 60 extends from a proximal bend point 70 to a distal bend point 72, having curved portion 60 therebetween. The curvedly tapered region in one embodiment is substantially non-linearly distally decreasing. In one embodiment, curved portion 60 has a shape described by a parabola. In another embodiment, curved portion 60 has a shape described by a logarithmic function. In a preferred embodiment, the surface of curve 60 changes less per unit distance with increasing distal position, having a steeper slope near proximal bend point 70. Applicants believe curved taper 60 provides an orderly transition for the suspended beads or particles being forced into the hypodermic needle. Applicants believe the curved transition region substantially lessens the occurrence of particles jamming together and blocking or substantially increasing the back pressure in lumen 48. Applicants have experienced blockage when attempting to inject a solid suspension through a fitting having a straight taper rather than a curved taper. The particles were observed to bunch together near the taper distal end, preventing further passage of particles and creating large back-pressure in the lumen, in response to continued applied syringe plunger pressure.

In use, the user can select an appropriate needle length to use and an appropriate solid suspension. After inserting and positioning an endoscope, the targeted site can be visualized and identified. A preferred use of the present invention is augmenting soft tissue with injected solid particles. While a preferred method utilizes an endoscope, other visualization methods such as fluoroscopy are also within the scope of the invention. Syringe 22 can be filled with an appropriate amount of solid suspension. Hypodermic needle assembly 24 can be filled with the solid suspension or other inert fluid and inserted into the endoscope. In a preferred method, hub wings 54 are properly oriented so as to properly orient needle skived portion 64 so as to optimally pierce the targeted site, such as a sphincter mechanism.

Syringe 22 can be secured to hypodermic needle assembly 24 by inserting syringe 22 into hub lumen 48 and rotating syringe 22 relative to hub 42 while holding hub wings 54 firmly. In one method, syringe and hub are secured together after the needle has been inserted into the endoscope. In another method, syringe and hub are secured together prior to inserting the hypodermic needle into the endoscope. Using the endoscope, needle distal skived portion 64 can be incrementally moved into position and into the targeted site in a sphincter mechanism. The rounded hub wings of the preferred embodiment should provide resistance to the needle being dislodged, should the wings be jarred during advancement through the endoscope, such as during an inadvertent collision with the endoscope eyepiece.

Once in place, suspended solids can be injected into the target site. The wings and multiple threads of the preferred embodiment provide structure to enable the formation of a tight, pressure resistant seal between syringe and needle hub. The curved taper of the present invention provides resistance to blockage which can be caused by the accumulation of the particles to be injected. The needle can be repeatedly retracted and advanced into multiple tissue sites proximate a location until treatment is complete. The needle and endoscope can then be withdrawn.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method for injecting suspensions of solids in liquids into a body comprising:

providing a needle having a longitudinal axis including a distal end for ejecting fluid, a proximal end for receiving fluid, and a lumen therethrough, and a Luer-lock fitting disposed on said needle proximal end having a generally cylindrical body, a distal end, a proximal end, a lumen therethrough, and a cylinder wall, said proximal end cylinder wall having a threaded region therein, said lumen having a curvedly tapered inside diameter;

providing a syringe having a plunger and threads adapted to mate to said Luer-lock fitting;

providing a suspension of solids within said syringe;

attaching said syringe to said Luer-lock fitting;

positioning said needle distal end into a target body location; and injecting said suspension from said syringe through said curved taper, through said needle lumen, and into said body target.

2. A method as recited in claim 1 wherein said solids have an average diameter of at least about 80 microns.

3. A method as recited in claim 1 wherein said Luer-lock fitting threaded region includes at least two threads, such that a higher pressure connection relative to a single thread fitting between said Luer-lock fitting and said syringe can be formed.

4. A method as recited in claim 3 wherein said Luer-lock fitting includes at least two wings extending outwardly from said longitudinal axis, said wings having a rounded periphery, such that an object striking said rounded wings has a tendency to glance off said wings, and said attaching step includes holding said wings while rotating said syringe and Luer-lock fitting relative to one another.

* * * * *